(12) United States Patent
Peretz

(10) Patent No.: US 12,186,174 B2
(45) Date of Patent: Jan. 7, 2025

(54) ONE-TIME USE ONLY COVER FOR MEDICAL APPLIANCE

(71) Applicant: Liron Peretz, Givatayim (IL)

(72) Inventor: Liron Peretz, Givatayim (IL)

( * ) Notice: Subject to any disclaimer, the term of this patent is extended or adjusted under 35 U.S.C. 154(b) by 0 days.

(21) Appl. No.: 17/641,922

(22) PCT Filed: Nov. 11, 2020

(86) PCT No.: PCT/IL2020/051167
§ 371 (c)(1),
(2) Date: Mar. 10, 2022

(87) PCT Pub. No.: WO2021/048865
PCT Pub. Date: Mar. 18, 2021

(65) Prior Publication Data
US 2022/0265491 A1    Aug. 25, 2022

(30) Foreign Application Priority Data

Sep. 11, 2019   (IL) .......................................... 269266

(51) Int. Cl.
*A61F 15/00*   (2006.01)
*A61F 13/04*   (2006.01)

(52) U.S. Cl.
CPC .......... *A61F 15/004* (2013.01); *A61F 13/043* (2013.01)

(58) Field of Classification Search
CPC .... A61F 15/004; A61F 13/041; A61F 13/043; A61F 2013/00165; A41D 13/08; A41D 13/081; A41D 13/088; A61B 42/00; A61B 42/10; A61B 46/27
See application file for complete search history.

(56) References Cited

U.S. PATENT DOCUMENTS

| 3,584,525 | A | * | 6/1971 | Caveney | ............... B65B 13/027 81/488 |
| 3,785,374 | A |   | 1/1974 | Lipson |  |
| 4,363,317 | A |   | 12/1982 | Broucek |  |
| 4,458,680 | A | * | 7/1984 | Childers | .............. A62B 17/006 2/457 |
| 5,342,286 | A | * | 8/1994 | Kelly | .................... A61F 15/004 602/62 |

(Continued)

FOREIGN PATENT DOCUMENTS

DE        4126139 A1    2/1993

OTHER PUBLICATIONS

PCT Search Report for International Application No. PCT/IL2020/051167, mailed Mar. 7, 2021, 1pp.

(Continued)

*Primary Examiner* — Keri J Nelson
(74) *Attorney, Agent, or Firm* — The Roy Gross Law Firm, LLC; Roy Gross

(57) ABSTRACT

A waterproof limb cover for preventing liquid ingress to a predefined region of a limb comprising a casing with at least one opening, into which a limb can be inserted. The casing, which is impermeable to the liquid, has at least one sealing closure mechanism to sealingly enclose a predefined region of the limb. The casing further comprises at least one predefined irreversibly rupturable region. Rupture of the irreversibly rupturable region allows removal of the waterproof limb cover from the limb, and prevents undesirable reuse of the cover.

17 Claims, 9 Drawing Sheets

(56) References Cited

U.S. PATENT DOCUMENTS

| | | | |
|---|---|---|---|
| 5,592,953 A | 1/1997 | Delao | |
| 8,056,148 B1* | 11/2011 | Ballantyne | A41D 13/08 |
| | | | 2/160 |
| 10,874,561 B1* | 12/2020 | Murphy | A61F 15/002 |
| 2004/0199974 A1 | 10/2004 | Fancher | |
| 2009/0182252 A1* | 7/2009 | Bennett | A61F 15/004 |
| | | | 602/3 |
| 2009/0287122 A1* | 11/2009 | Evans | A61F 15/004 |
| | | | 602/3 |
| 2009/0299240 A1 | 12/2009 | Brown et al. | |
| 2011/0087144 A1 | 4/2011 | Lee et al. | |
| 2013/0091612 A1* | 4/2013 | Grassano | A41D 13/088 |
| | | | 2/16 |
| 2013/0224346 A1* | 8/2013 | Cheema | B65D 75/5844 |
| | | | 229/87.08 |
| 2015/0290053 A1 | 10/2015 | Loughney et al. | |
| 2017/0049603 A1* | 2/2017 | Lambert | A61F 5/05866 |
| 2017/0189248 A1 | 7/2017 | Brown et al. | |

OTHER PUBLICATIONS

PCT Written Opinion for International Application No. PCT/IL2020/051167, mailed Mar. 7, 2021, 1pp.

\* cited by examiner

ONE-TIME USE ONLY COVER FOR MEDICAL APPLIANCE

CROSS REFERENCE TO RELATED APPLICATIONS

This application is a National Phase of PCT Patent Application No. PCT/IL2020/051167 having International filing date of Nov. 11, 2020, which claims the benefit of priority of Israeli Patent Application No. 269266, filed Sep. 11, 2019, the contents of which are all incorporated herein by reference in their entirety.

FIELD OF THE INVENTION

The present invention generally pertains to a system and method for providing a non-reusable, one-time use only, waterproof cover for a cast, bandage or other medical appliance.

BACKGROUND OF THE INVENTION

Casts, bandages and other medical appliances are typically permeable, to water, to water vapor and often to both. However, too much exposure to water can weaken the material from which the appliance is made, necessitating repair or replacement of the appliance, or can allow permeation of water to the lesion being protected, necessitating replacement of the appliance and, often re-sterilization of the lesion. The need for repair, preplacement and/or sterilization is inconvenient (and can be dangerous) for the patient and requires expenditure of medical professionals' time. However, any medical appliance which remains in place for more than a day or so is likely to be exposed to water, as the patient is likely to need to bathe or shower or to want to want to swim during this period. Therefore, an impermeable cover which prevents an ingress of water to the area of the cast or bandage during bathing, showering or swimming would be indicated.

In some cases, such as a cast cover for personal use be a patient during a holiday, reuse of such a cover can be advantageous. Under other circumstances, such as within a hospital or for a wound producing exudates, the cover must be single-use only.

There are a large number of commercially-available cast covers on the market. A few of names include: Bloccs, Mighty-X, Vive, Doact, Seal-Tight, DryPro, TKWC, UpGoing and Disposable Shower SOC; there are many others. Most comprise a casing open at one end and closed at the other end, with a closure mechanism at the open end. A few have a casing open at both ends with a closure mechanism at each end. For all of them, at least the portion of the casing material away from the open end(s) is flexible. Closure mechanisms include: an elastic top, an elastic rubber seal with pull tabs, a diaphragm seal, a vacuum seal (the entire interior of the casing is placed under vacuum), and a vacuum ring (only a ring at the opening is placed under vacuum). Most of the commercially-available cast covers are intended to be re-used, often for weeks or months. The remainder, although they may be intended for single use, are reusable "if removed carefully". Removal is typically by reversing the procedure used to put the cast protector on or by rolling the cast cover down the limb.

U.S. Pat. No. 3,785,374 discloses an elongated, waterproof, flexible casing having an opening at one end through which a cast-bound limb is inserted and sealing means around the opening including an inflatable cuff of substantially toroidal configuration and sufficiently wide to distribute the sealing pressure over a large enough area to prevent interference with the blood supply to the injured limb when the cuff is inflated. Longitudinally oriented flotation sections may be disposed in the wall of the casing to further aid in buoying up the cast-bound limb while swimming and/or for therapeutic water treatments.

In normal use, the waterproof flexible casing is removed without damaging it.

U.S. Pat. No. 4,363,317 discloses a watertight cast cover for protecting a cast, bandage or the like includes an elongated, generally tubular waterproof member having a closed end and an open end. An adjustable resilient sealing band extends around the periphery of the open end of the member. The band includes overlapping ends, one end of which defines a flap. The flap and band may be stretched to form a seal with the user's limb and the flap is securable to the band.

In normal use, the cast cover is removed without damaging it.

U.S. patent application publication no. US2009/299240 discloses a cast and bandage protector that avoids use of a sealing ring and therefore can be folded over upon itself, has suitability for convenient packaging and at the same time still provides an effective waterproof sealing arrangement. The sealing mechanism is a stretchable diaphragm glued to the open end of the casing.

In normal use, the cast protector is removed without damaging it.

U.S. patent application publication no. US2015290053 discloses an apparatus to protect a limb having a wound or condition requiring dryness from moisture. The method of applying a protective covering for a wound or condition requiring dryness comprising the steps of positioning a waterproof polyester fabric sock around an appendage having a gasket secured to an open end of the sock for sealing the sock to an appendage.

In normal use, the polyester fabric sock is removed without damaging it.

U.S. patent application publication no. US2017/189248 discloses a cast and bandage protector that uses a seal ring but avoids water pooling and seepage. It uses a flexible, stretchable and deformable diaphragm stretched tightly over a seal ring in order to seal the ordinarily open end of a flexible sleeve of waterproof material. The rigid seal ring flexible holder holds the flexible sleeve open and the diaphragm tightly stretches over and above it to minimize water pooling seepage and leaking about the interface of the diaphragm and the limb of the patient wearing the cast and the cast protector.

It is therefore a long felt need to provide a wound or cast protector that is for one-time use only, as it can not be removed as a reusable unit.

SUMMARY OF THE INVENTION

It is an object of the present invention to disclose a system for providing a one-time use only, non-reusable waterproof limb cover for a cast, bandage or other medical appliance.

It is another object of the present invention to disclose a waterproof limb cover for preventing liquid ingress to a predefined region of a limb, comprising:

a casing impermeable to said liquid, said casing comprising at least one opening, said at least one opening for insertion of said limb, said opening comprising at least one sealing closure mechanism configured to sealingly enclose said predefined region of said limb;

wherein said waterproof limb cover further comprises at least one predefined irreversibly rupturable region for removal of said waterproof limb cover from said predefined region of said limb.

It is another object of the present invention to disclose the waterproof limb cover as described above, wherein said at least one sealing closure mechanism comprises a one-way mechanism.

It is another object of the present invention to disclose the waterproof limb cover as described above, wherein said at least one sealing closure mechanism comprises a member selected from a group consisting of an elasticated region, a fastenable string or tape, a diaphragm seal, an inflatable cuff, a vacuum ring, an adhesive region, a hook and loop closure, a buckle and strap and any combination thereof.

It is another object of the present invention to disclose the waterproof limb cover as described above, wherein said one-way mechanism comprises at least one member of a group consisting of a one-way ratchet and pawl, a one-way gear track and pawl, a one-way hook and loop, a one-way valve, a permanent adhesive and a release layer between an edge of the waterproof limb cover and the predefined region of said limb.

It is another object of the present invention to disclose the waterproof limb cover as described above, wherein said waterproof limb cover comprises medical-grade material.

It is another object of the present invention to disclose the waterproof limb cover as described above, wherein said casing comprises a material selected from a group consisting of polyvinyl chloride, polyurethane, polyethylene, polyethylene terephthalate, polypropylene, polystyrene and any combination thereof.

It is another object of the present invention to disclose the waterproof limb cover as described above, wherein said casing comprises a material selected from a group consisting of: a printable material, a pigmentable material, a texturable material, a scorable material and any combination thereof.

It is another object of the present invention to disclose the waterproof limb cover as described above, wherein said casing is configured to display at least one indicia, said indicia selected from a group consisting of: a logo, a name, a patient datum, a hospital datum, a ward indicator, a location indicator, a best-before indicator, a picture, an illustration and any combination thereof.

It is another object of the present invention to disclose the waterproof limb cover as described above, additionally comprising a reversibly closable side opening.

It is another object of the present invention to disclose the waterproof limb cover as described above, wherein a size and shape of said reversibly closable side opening is inadequate to permit removal of said waterproof limb cover from said predefined region of said limb.

It is another object of the present invention to disclose the waterproof limb cover as described above, wherein at least one of said at least one predefined irreversibly rupturable region extends to an edge of said waterproof limb cover.

It is another object of the present invention to disclose the waterproof limb cover as described above, wherein rupture of at least one of said at least one predefined irreversibly rupturable region ruptures at least one of said at least one sealing closure mechanism.

It is another object of the present invention to disclose the waterproof limb cover as described above, wherein said at least one predefined irreversibly rupturable region comprises at least one member of a group consisting of a tear strip, a tear line, a score line, a perforation and a weakened region.

It is another object of the present invention to disclose the waterproof limb cover as described above, wherein said tear strip remains attached to said waterproof limb cover in at least one area after tearing, said waterproof limb cover and said tear strip being necessarily disposable as a unit.

It is another object of the present invention to disclose the waterproof limb cover as described above, wherein said tear strip comprises an insert of a material having at least one property with a value different from a same property of said casing material.

It is another object of the present invention to disclose the waterproof limb cover as described above, wherein said at least one property of said insert is selected from a group consisting of a greater stiffness than said casing material, a greater strength than said casing material, a greater elasticity than said casing material and any combination thereof It is another object of the present invention to disclose the waterproof limb cover as described above, wherein said weakened region consists of a member of a group consisting of a region with thinner material than said casing material, a region of material with a lower tear strength than said casing material, and any combination thereof.

It is another object of the present invention to disclose the waterproof limb cover as described above, wherein said waterproof limb cover comprises, in or near at least one of said at least one predefined irreversibly rupturable region, a pullable member selected from a group consisting of a tag, a ring, a protrusion and any combination thereof.

It is another object of the present invention to disclose the waterproof limb cover as described above, wherein pulling on said pullable member ruptures at least a portion of said predefined irreversibly rupturable region.

It is another object of the present invention to disclose the waterproof limb cover as described above, wherein at least one edge of said waterproof limb cover comprises, in or near at least one of said at least one predefined irreversibly rupturable region, a tear initiator selected from a group consisting of a notch, a gap and any combination thereof.

It is another object of the present invention to disclose the waterproof limb cover as described above, wherein separation of edges of said tear initiator initiates tearing of said at least one of said at least one predefined irreversibly rupturable region.

It is another object of the present invention to disclose the waterproof limb cover as described above, wherein said limb is a limb of a non-human animal.

It is another object of the present invention to disclose the waterproof limb cover as described above, wherein said non-human animal is selected from a group consisting of: a non-human primate, an equine, a feline, a canine, a cow, a sheep, a goat, a llama, and a pig.

It is another object of the present invention to disclose the waterproof limb cover as described above, wherein said waterproof limb cover is providable in a packaging selected from a group consisting of aseptic packaging and sterile packaging.

It is another object of the present invention to disclose the waterproof limb cover as described above, wherein said waterproof limb cover is configured to cover a member of a group consisting of a cast, a wound, a burn, a dermatological condition and any combination thereof.

It is another object of the present invention to disclose the waterproof limb cover as described above, wherein said dermatological condition is selected from a group consisting of a fungal infection, psoriasis, eczema and any combination thereof.

It is another object of the present invention to disclose the waterproof limb cover as described above, additionally comprising a stiffening mechanism.

It is another object of the present invention to disclose the waterproof limb cover as described above, wherein said irreversibly rupturable region comprises said stiffening mechanism.

It is another object of the present invention to disclose the waterproof limb cover as described above, wherein said stiffening mechanism has a form selected from a group consisting of a spiral, a loop and any combination thereof.

It is another object of the present invention to disclose the waterproof limb cover as described above, wherein said stiffening mechanism comprises a plurality of loops.

It is another object of the present invention to disclose the waterproof limb cover as described above, wherein said plurality of loops are either all the same size or at least two of said loops are of different sizes.

It is another object of the present invention to disclose the waterproof limb cover as described above, wherein a material of said stiffening mechanism is selected from a group consisting of spring steel, plastic strip, wire, and any combination thereof.

It is another object of the present invention to disclose a method of removing a waterproof limb cover from a predefined region of a limb, comprising steps of:
providing a waterproof limb cover for preventing liquid ingress to a predefined region of a limb, comprising:
a casing impermeable to said liquid, said casing comprising at least one opening, said at least one opening for insertion of said limb, said opening comprising at least one sealing closure mechanism configured to sealingly enclose said predefined region of said limb; and
at least one predefined irreversibly rupturable region;
emplacing said waterproof limb cover around said predefined region of said limb, said waterproof limb cover and completely covering said predefined region of said limb;
sealingly closing all said at least one sealing closure mechanism and sealingly enclosing said predefined region of said limb;
rupturing said at least one predefined irreversibly rupturable region, thereby irreversibly damaging said waterproof limb cover; and
removing said waterproof limb cover from said limb.

It is another object of the present invention to disclose the method as described above, additionally comprising a step of providing said at least one sealing closure mechanism comprising a one-way mechanism.

It is another object of the present invention to disclose the method as described above, additionally comprising a step of selecting said at least one sealing closure mechanism comprising a member of a group consisting of an elasticated region, a fastenable string or tape, a diaphragm seal, an inflatable cuff, a vacuum ring, an adhesive region, a hook and loop closure, a buckle and strap and any combination thereof.

It is another object of the present invention to disclose the method as described above, additionally comprising a step of providing said one-way mechanism comprising at least one member of a group consisting of a one-way ratchet and pawl, a one-way gear track and pawl, a one-way hook and loop, a one-way valve, a permanent adhesive and a release layer between an edge of the waterproof limb cover and said predefined region of said limb.

It is another object of the present invention to disclose the method as described above, additionally comprising a step of providing said waterproof limb cover comprising medical-grade material.

It is another object of the present invention to disclose the method as described above, additionally comprising a step of providing said casing comprising a material selected from a group consisting of polyvinyl chloride, polyurethane, polyethylene, polyethylene terephthalate, polypropylene, polystyrene and any combination thereof.

It is another object of the present invention to disclose the method as described above, additionally comprising a step of providing said casing comprising a material selected from a group consisting of: a printable material, a pigmentable material, a texturable material, a scorable material and any combination thereof.

It is another object of the present invention to disclose the method as described above, additionally comprising a step of displaying at least one indicia on said casing, said indicia selected from a group consisting of: a logo, a name, a patient datum, a hospital datum, a ward indicator, a location indicator, a best-before indicator, a picture, an illustration and any combination thereof.

It is another object of the present invention to disclose the method as described above, additionally comprising a step of providing said waterproof limb cover with a reversibly closable side opening.

It is another object of the present invention to disclose the method as described above, additionally comprising a step of selecting a size and shape of said reversibly closable side opening to be inadequate to permit removal of said waterproof limb cover from said predefined region of said limb.

It is another object of the present invention to disclose the method as described above, additionally comprising a step of providing at least one of said at least one predefined irreversibly rupturable region extending to an edge of said waterproof limb cover.

It is another object of the present invention to disclose the method as described above, additionally comprising a step of rupturing at least one of said at least one sealing closure mechanism by rupturing at least one of said at least one predefined irreversibly rupturable region.

It is another object of the present invention to disclose the method as described above, additionally comprising a step of providing said at least one predefined irreversibly rupturable region comprising at least one member of a group consisting of a tear strip, a tear line, a score line, a perforation and a weakened region.

It is another object of the present invention to disclose the method as described above, additionally comprising a step providing said waterproof limb cover and said tear strip necessarily disposable as a unit, said tear strip remaining attached to said waterproof limb cover in at least one area after tearing.

It is another object of the present invention to disclose the method as described above, additionally comprising a step of providing said tear strip comprising an insert of a material having at least one property with a value different from a same property of said casing material.

It is another object of the present invention to disclose the method as described above, additionally comprising a step of selecting said at least one property of said insert from a group consisting of a greater stiffness than said casing material, a greater strength than said casing material, a greater elasticity than said casing material and any combination thereof.

It is another object of the present invention to disclose the method as described above, additionally comprising a step of providing said weakened region comprising a member of a group consisting of a region with thinner material than said casing material, a region of material with a lower tear strength than said casing material, and any combination thereof.

It is another object of the present invention to disclose the method as described above, additionally comprising a step of providing said waterproof limb cover comprising, in or near at least one of said at least one predefined irreversibly rupturable region, a pullable member selected from a group consisting of a tag, a ring, a protrusion and any combination thereof.

It is another object of the present invention to disclose the method as described above, additionally comprising a step of pulling on said pullable member and rupturing at least a portion of said predefined irreversibly rupturable region.

It is another object of the present invention to disclose the method as described above, additionally comprising a step of providing at least one edge of said waterproof limb cover comprising, in or near at least one of said at least one predefined irreversibly rupturable region, a tear initiator selected from a group consisting of a notch, a gap and any combination thereof.

It is another object of the present invention to disclose the method as described above, additionally comprising a step of initiating tearing of said at least one of said at least one predefined irreversibly rupturable region by separating edges of said tear initiator.

It is another object of the present invention to disclose the method as described above, additionally comprising a step of selecting said limb to be a limb of a non-human animal.

It is another object of the present invention to disclose the method as described above, additionally comprising a step of selecting said non-human animal from a group consisting of: a non-human primate, an equine, a feline, a canine, a cow, a sheep, a goat, a llama, and a pig.

It is another object of the present invention to disclose the method as described above, additionally comprising a step of providing said waterproof limb cover in a packaging selected from a group consisting of aseptic packaging and sterile packaging.

It is another object of the present invention to disclose the method as described above, additionally comprising a step of said waterproof limb cover covering a member of a group consisting of a cast, a wound, a burn, a dermatological condition and any combination thereof.

It is another object of the present invention to disclose the method as described above, additionally comprising a step of selecting said dermatological condition from a group consisting of a fungal infection, psoriasis, eczema and any combination thereof.

It is another object of the present invention to disclose the method as described above, additionally comprising a step of providing a stiffening mechanism.

It is another object of the present invention to disclose the method as described above, additionally comprising a step of comprising said stiffening mechanism within said irreversibly rupturable region.

It is another object of the present invention to disclose the method as described above, additionally comprising a step of selecting a form of said stiffening mechanism from a group consisting of a spiral, a loop and any combination thereof.

It is another object of the present invention to disclose the method as described above, additionally comprising a step of providing said stiffening mechanism comprising a plurality of loops.

It is another object of the present invention to disclose the method as described above, additionally comprising a step of providing said plurality of loops either all the same size or at least two of said loops of different sizes.

It is another object of the present invention to disclose the method as described above, additionally comprising a step of selecting a material of said stiffening mechanism from a group consisting of spring steel, plastic strip, wire, and any combination thereof.

It is another object of the present invention to disclose a waterproof limb cover for preventing liquid ingress to a predefined region of a limb of a non-human animal, comprising:
    a casing impermeable to said liquid, said casing comprising at least one opening, said at least one opening for insertion of said limb, said opening comprising at least one sealing closure mechanism configured to sealingly enclose said predefined region of said limb;
    wherein said waterproof limb cover further comprises at least one predefined irreversibly rupturable region for removal of said waterproof limb cover from said predefined region of said limb.

It is another object of the present invention to disclose the waterproof limb cover as described above, wherein said non-human animal is selected from a group consisting of: a non-human primate, an equine, a feline, a canine, a cow, a sheep, a goat, a llama, and a pig.

It is another object of the present invention to disclose the waterproof limb cover as described above, wherein said at least one sealing closure mechanism comprises a one-way mechanism.

It is another object of the present invention to disclose the waterproof limb cover as described above, wherein said at least one sealing closure mechanism comprises a member selected from a group consisting of an elasticated region, a fastenable string or tape, a diaphragm seal, an inflatable cuff, a vacuum ring, an adhesive region, a hook and loop closure, a buckle and strap and any combination thereof.

It is another object of the present invention to disclose the waterproof limb cover as described above, wherein said one-way mechanism comprises at least one member of a group consisting of a one-way ratchet and pawl, a one-way gear track and pawl, a one-way hook and loop, a one-way valve, a permanent adhesive and a release layer between an edge of the waterproof limb cover and the predefined region of said limb.

It is another object of the present invention to disclose the waterproof limb cover as described above, wherein said waterproof limb cover comprises medical-grade material.

It is another object of the present invention to disclose the waterproof limb cover as described above, wherein said casing comprises a material selected from a group consisting of polyvinyl chloride, polyurethane, polyethylene, polyethylene terephthalate, polypropylene, polystyrene and any combination thereof.

It is another object of the present invention to disclose the waterproof limb cover as described above, wherein said casing comprises a material selected from a group consisting of: a printable material, a pigmentable material, a texturable material, a scorable material and any combination thereof.

It is another object of the present invention to disclose the waterproof limb cover as described above, wherein said casing is configured to display at least one indicia, said indicia selected from a group consisting of: a logo, a name, a patient datum, a hospital datum, a ward indicator, a location indicator, a best-before indicator, a picture, an illustration and any combination thereof.

It is another object of the present invention to disclose the waterproof limb cover as described above, additionally comprising a reversibly closable side opening.

It is another object of the present invention to disclose the waterproof limb cover as described above, wherein a size and shape of said reversibly closable side opening is inadequate to permit removal of said waterproof limb cover from said predefined region of said limb.

It is another object of the present invention to disclose the waterproof limb cover as described above, wherein at least one of said at least one predefined irreversibly rupturable region extends to an edge of said waterproof limb cover.

It is another object of the present invention to disclose the waterproof limb cover as described above, wherein rupture of at least one of said at least one predefined irreversibly rupturable region ruptures at least one of said at least one sealing closure mechanism.

It is another object of the present invention to disclose the waterproof limb cover as described above, wherein said at least one predefined irreversibly rupturable region comprises at least one member of a group consisting of a tear strip, a tear line, a score line, a perforation and a weakened region.

It is another object of the present invention to disclose the waterproof limb cover as described above, wherein said tear strip remains attached to said waterproof limb cover in at least one area after tearing, said waterproof limb cover and said tear strip being necessarily disposable as a unit.

It is another object of the present invention to disclose the waterproof limb cover as described above, wherein said tear strip comprises an insert of a material having at least one property with a value different from a same property of said casing material.

It is another object of the present invention to disclose the waterproof limb cover as described above, wherein said at least one property of said insert is selected from a group consisting of a greater stiffness than said casing material, a greater strength than said casing material, a greater elasticity than said casing material and any combination thereof.

It is another object of the present invention to disclose the waterproof limb cover as described above, wherein said weakened region consists of a member of a group consisting of a region with thinner material than said casing material, a region of material with a lower tear strength than said casing material, and any combination thereof.

It is another object of the present invention to disclose the waterproof limb cover as described above, wherein said waterproof limb cover comprises, in or near at least one of said at least one predefined irreversibly rupturable region, a pullable member selected from a group consisting of a tag, a ring, a protrusion and any combination thereof.

It is another object of the present invention to disclose the waterproof limb cover as described above, wherein pulling on said pullable member ruptures at least a portion of said predefined irreversibly rupturable region.

It is another object of the present invention to disclose the waterproof limb cover as described above, wherein at least one edge of said waterproof limb cover comprises, in or near at least one of said at least one predefined irreversibly rupturable region, a tear initiator selected from a group consisting of a notch, a gap and any combination thereof.

It is another object of the present invention to disclose the waterproof limb cover as described above, wherein separation of edges of said tear initiator initiates tearing of said at least one of said at least one predefined irreversibly rupturable region.

It is another object of the present invention to disclose the waterproof limb cover as described above, wherein said waterproof limb cover is providable in a packaging selected from a group consisting of aseptic packaging and sterile packaging.

It is another object of the present invention to disclose the waterproof limb cover as described above, wherein said waterproof limb cover is configured to cover a member of a group consisting of a cast, a wound, a burn, a dermatological condition and any combination thereof.

It is another object of the present invention to disclose the waterproof limb cover as described above, wherein said dermatological condition is selected from a group consisting of a fungal infection, psoriasis, eczema and any combination thereof.

It is another object of the present invention to disclose the waterproof limb cover as described above, additionally comprising a stiffening mechanism.

It is another object of the present invention to disclose the waterproof limb cover as described above, wherein said irreversibly rupturable region comprises said stiffening mechanism.

It is another object of the present invention to disclose the waterproof limb cover as described above, wherein said stiffening mechanism has a form selected from a group consisting of a spiral, a loop and any combination thereof.

It is another object of the present invention to disclose the waterproof limb cover as described above, wherein said stiffening mechanism comprises a plurality of loops.

It is another object of the present invention to disclose the waterproof limb cover as described above, wherein said plurality of loops are either all the same size or at least two of said loops are of different sizes.

It is another object of the present invention to disclose the waterproof limb cover as described above, wherein a material of said stiffening mechanism is selected from a group consisting of spring steel, plastic strip, wire, and any combination thereof.

It is another object of the present invention to disclose a method of removing a waterproof limb cover from a predefined region of a limb, comprising steps of:
  providing a waterproof limb cover for preventing liquid ingress to a predefined region of a limb, comprising:
    a casing impermeable to said liquid, said casing comprising at least one opening, said at least one opening for insertion of said limb, said opening comprising at least one sealing closure mechanism configured to sealingly enclose said predefined region of said limb; and
    at least one predefined irreversibly rupturable region;
  emplacing said waterproof limb cover around said predefined region of said limb, said waterproof limb cover and completely covering said predefined region of said limb;
  sealingly closing all said at least one sealing closure mechanism and sealingly enclosing said predefined region of said limb;
  rupturing said at least one predefined irreversibly rupturable region, thereby irreversibly damaging said waterproof limb cover; and
  removing said waterproof limb cover from said limb.

It is another object of the present invention to disclose the method as described above, additionally comprising a step of selecting said non-human animal from a group consisting of: a non-human primate, an equine, a feline, a canine, a cow, a sheep, a goat, a llama, and a pig.

It is another object of the present invention to disclose the method as described above, additionally comprising a step of providing said at least one sealing closure mechanism comprising a one-way mechanism.

It is another object of the present invention to disclose the method as described above, additionally comprising a step of selecting said at least one sealing closure mechanism comprising a member of a group consisting of an elasticated region, a fastenable string or tape, a diaphragm seal, an inflatable cuff, a vacuum ring, an adhesive region, a hook and loop closure, a buckle and strap and any combination thereof.

It is another object of the present invention to disclose the method as described above, additionally comprising a step of providing said one-way mechanism comprising at least one member of a group consisting of a one-way ratchet and pawl, a one-way gear track and pawl, a one-way hook and loop, a one-way valve, a permanent adhesive and a release layer between an edge of the waterproof limb cover and said predefined region of said limb.

It is another object of the present invention to disclose the method as described above, additionally comprising a step of providing said waterproof limb cover comprising medical-grade material.

It is another object of the present invention to disclose the method as described above, additionally comprising a step of providing said casing comprising a material selected from a group consisting of polyvinyl chloride, polyurethane, polyethylene, polyethylene terephthalate, polypropylene, polystyrene and any combination thereof.

It is another object of the present invention to disclose the method as described above, additionally comprising a step of providing said casing comprising a material selected from a group consisting of: a printable material, a pigmentable material, a texturable material, a scorable material and any combination thereof.

It is another object of the present invention to disclose the method as described above, additionally comprising a step of displaying at least one indicia on said casing, said indicia selected from a group consisting of: a logo, a name, a patient datum, a hospital datum, a ward indicator, a location indicator, a best-before indicator, a picture, an illustration and any combination thereof.

It is another object of the present invention to disclose the method as described above, additionally comprising a step of providing said waterproof limb cover with a reversibly closable side opening.

It is another object of the present invention to disclose the method as described above, additionally comprising a step of selecting a size and shape of said reversibly closable side opening to be inadequate to permit removal of said waterproof limb cover from said predefined region of said limb.

It is another object of the present invention to disclose the method as described above, additionally comprising a step of providing at least one of said at least one predefined irreversibly rupturable region extending to an edge of said waterproof limb cover.

It is another object of the present invention to disclose the method as described above, additionally comprising a step of rupturing at least one of said at least one sealing closure mechanism by rupturing at least one of said at least one predefined irreversibly rupturable region.

It is another object of the present invention to disclose the method as described above, additionally comprising a step of providing said at least one predefined irreversibly rupturable region comprising at least one member of a group consisting of a tear strip, a tear line, a score line, a perforation and a weakened region.

It is another object of the present invention to disclose the method as described above, additionally comprising a step providing said waterproof limb cover and said tear strip necessarily disposable as a unit, said tear strip remaining attached to said waterproof limb cover in at least one area after tearing.

It is another object of the present invention to disclose the method as described above, additionally comprising a step of providing said tear strip comprising an insert of a material having at least one property with a value different from a same property of said casing material.

It is another object of the present invention to disclose the method as described above, additionally comprising a step of selecting said at least one property of said insert from a group consisting of a greater stiffness than said casing material, a greater strength than said casing material, a greater elasticity than said casing material and any combination thereof.

It is another object of the present invention to disclose the method as described above, additionally comprising a step of providing said weakened region comprising a member of a group consisting of a region with thinner material than said casing material, a region of material with a lower tear strength than said casing material, and any combination thereof.

It is another object of the present invention to disclose the method as described above, additionally comprising a step of providing said waterproof limb cover comprising, in or near at least one of said at least one predefined irreversibly rupturable region, a pullable member selected from a group consisting of a tag, a ring, a protrusion and any combination thereof.

It is another object of the present invention to disclose the method as described above, additionally comprising a step of pulling on said pullable member and rupturing at least a portion of said predefined irreversibly rupturable region.

It is another object of the present invention to disclose the method as described above, additionally comprising a step of providing at least one edge of said waterproof limb cover comprising, in or near at least one of said at least one predefined irreversibly rupturable region, a tear initiator selected from a group consisting of a notch, a gap and any combination thereof.

It is another object of the present invention to disclose the method as described above, additionally comprising a step of initiating tearing of said at least one of said at least one predefined irreversibly rupturable region by separating edges of said tear initiator.

It is another object of the present invention to disclose the method as described above, additionally comprising a step of providing said waterproof limb cover in a packaging selected from a group consisting of aseptic packaging and sterile packaging.

It is another object of the present invention to disclose the method as described above, additionally comprising a step of said waterproof limb cover covering a member of a group consisting of a cast, a wound, a burn, a dermatological condition and any combination thereof.

It is another object of the present invention to disclose the method as described above, additionally comprising a step of selecting said dermatological condition from a group consisting of a fungal infection, psoriasis, eczema and any combination thereof.

It is another object of the present invention to disclose the method as described above, additionally comprising a step of providing a stiffening mechanism.

It is another object of the present invention to disclose the method as described above, additionally comprising a step of comprising said stiffening mechanism within said irreversibly rupturable region.

It is another object of the present invention to disclose the method as described above, additionally comprising a step of selecting a form of said stiffening mechanism from a group consisting of a spiral, a loop and any combination thereof.

It is another object of the present invention to disclose the method as described above, additionally comprising a step of providing said stiffening mechanism comprising a plurality of loops.

It is another object of the present invention to disclose the method as described above, additionally comprising a step of providing said plurality of loops either all the same size or at least two of said loops of different sizes.

It is another object of the present invention to disclose the method as described above, additionally comprising a step of selecting a material of said stiffening mechanism from a group consisting of spring steel, plastic strip, wire, and any combination thereof.

BRIEF DESCRIPTION OF THE FIGURES

In order to better understand the invention and its implementation in practice, a plurality of embodiments will now be described, by way of non-limiting example only, with reference to the accompanying drawings, wherein.

DETAILED DESCRIPTION OF THE PREFERRED EMBODIMENTS

Figures 1A, 1B:
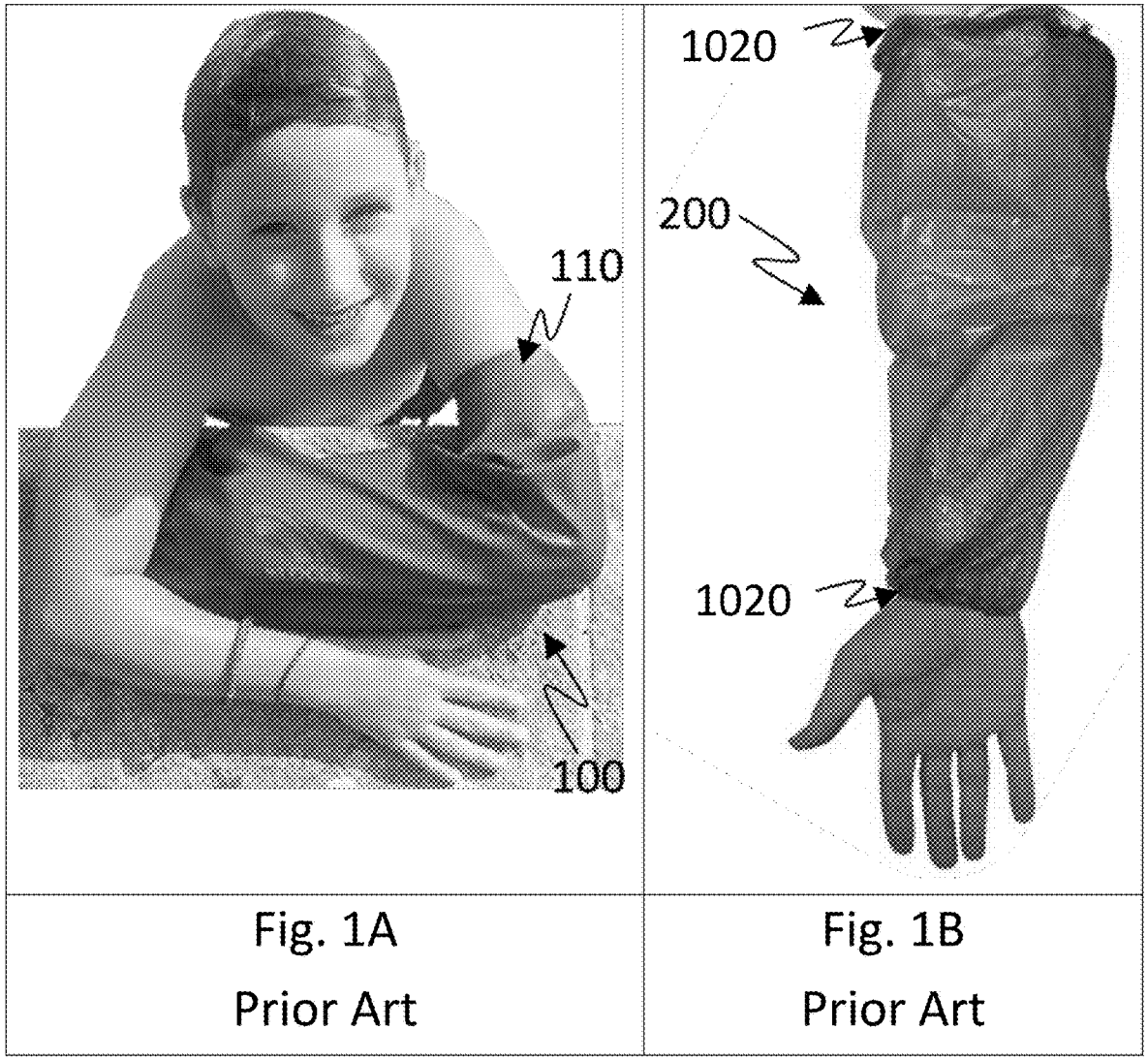
FIG. 1A-B illustrates the prior art.

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for providing a medical device, a one-time use only, non-reusable waterproof cover for a cast, bandage or other medical appliance.

In all of the prior art, the cast protector does not comprise a tearable predefined irreversibly rupturable region or other mechanism for ensuring that it is irreparably damaged during removal. In normal use, in the prior art, the cast protector is removed without damaging it.

A primary purpose of the waterproof cover of the present invention is that it provides a non-reusable waterproof cover for a cast or an area on a patient which must remain dry which is necessarily for one-time use only. During use, although other portions of the patient can get wet (e.g., by being bathed), the area protected by the waterproof cover of the present invention will remain dry. The waterproof cover is for one-time use only; at the end of use, the waterproof cover is necessarily damaged by removal so that it cannot be re-used, no matter how carefully it is removed. This can help prevent accidental transfer of infective material from one patient to another via material adhering to a reused cover.

The waterproof cover of the present invention comprises a flexible casing, open at least one end and typically either closed or closable at the opposite end, although it can be open at both ends. Each opening comprises a sealing closure mechanism to prevent, during use, ingress of liquid into the casing interior via the opening. The sealing closure mechanism can comprise an elasticated region, a fastenable string or tape, a diaphragm seal, an inflatable cuff, a vacuum ring, an adhesive region, a hook and loop closure, a buckle and strap or any other conventional means of sealing a casing against skin so as to prevent, during use, ingress of liquid into the casing interior via the opening, and any combination thereof.

The waterproof cover can be used as a cast cover, as a wound cover, as a cover for burns, and during treatment of dermatological conditions such as, but not limited to, fungal infections, psoriasis and eczema.

The waterproof cover is preferably provided packaged; preferably, the packaging is flexible, although rigid or semi-rigid packaging can be used. The packaged waterproof cover can be provided as either a sterile waterproof cover or as an aseptic waterproof cover. For use as, for non-limiting example, a cast cover, asepsis would be adequate. However, if the wound cover is the only protection for, for non-limiting example, a burn, then a sterile waterproof cover would be indicated.

For a sterile waterproof cover, the packaging should conform to at least one of ISO 11607-1 (Packaging for terminally sterilized medical devices—Part 1: Requirements for materials, sterile barrier systems and packaging systems) and ISO 11607-2 (Packaging for terminally sterilized medical devices—Part 2: Validation requirements for forming, sealing and assembly processes).

A sterile product can have been sterilized according to ISO 11135 (Sterilization of health-care products—Ethylene oxide), ISO 11137 and ISO/TS 13004 (Sterilization of health care products-Radiation), ISO 11138 (Sterilization of health care products—Biological indicators), 111 40 (Sterilization of health care products—Chemical indicators), ISO 11737 (Sterilization of health care products—Microbiological methods), ISO 17665 (Sterilization of health care products—Moist heat), ISO 20857 (Sterilization of health care products—Dry heat) and ISO 25424 (Sterilization of health care products—Low temperature steam and formaldehyde).

An aseptic waterproof cover should be processed according to ISO 13408 (Aseptic processing of health care products).

The waterproof cover can be configured for use on a human (adult or child) or on a non-human animal. Non-limiting examples of a non-human animal for which the wound cover can be used include a non-human primate, an equine, a feline, a canine, a cow, a sheep, a goat, a llama, and a pig.

The waterproof cover can be used in any setting where a sterile or aseptic and waterproof cover for a portion of a body is needed and, typically where it is important to ensure that the cover can not be re-used since re-use can lead to transmission of infection from one patient to a subsequent user. Such a setting can include, but is not limited to, a hospital for humans, a doctor's office, the home, a nursing home, a rehabilitation center, a hospice, a veterinary office, a veterinary surgery, a veterinary hospital, a zoo, a farm, a safari park, a ranch, or, for emergency use, the waterproof cover can be stored in (and used from) an ambulance, a medical backpack, an ambucycle, a rescue helicopter, a rescue boat, and a mobile hospital.

Since the waterproof cover of the present invention is single use only and is preferably delivered in an aseptic or sterile package, it provides an aseptic or sterile covering for a cast, a wound or other lesion, an area of damaged skin or an area of infected skin. Since the wound covering is waterproof and in sealing contact with the skin (or fur of an animal), the wound covering is hygienic, in the sense that external matter can not reach the enclosed area, in the sense that pathogens and infective matter from the enclosed area can not escape into the environment and in the sense that pathogens, bacteria or infective matter can not be transferred from one patient to another via a re-used wound cover.

It should also be noted that the wound cover can comprise material on which indicia can be inscribed or in which indicia can be included. Non-limiting examples of methods of applying indicia include printing on a material, infusing pigment into a material, scratching or scraping material so as to change its color, texture, reflectivity and any combination thereof, and adding material of a different color, texture, reflectivity and any combination thereof to a material. Added material can be a coating or an insertion within a material. The indicia can be a logo (for non-limiting example, a logo of a company or hospital), instructions for use, an indication of a location of a tear region, an indication of a location of a pull tab, an indication of the body portion on which it can be used, an indication of a function or place of use (e.g., for use in an emergency ward, for burn treatment, for antifungal treatment), a name or other identifier of a patient (e.g., the name of a pet), a name or other identifier of a treatment, a best-before indicator, a picture or illustration to make a patient feel more comfortable using the wound cover, and any combination thereof.

In various embodiments, the present invention can be used on a limb, torso or neck of a human or non-human animal, on the top and back of the skull of human or a non-human animal. In less-preferred embodiments, it can protect at least a portion of an inanimate object which has a smaller-diameter area encirclable by an opening sealingly closable by a sealing closure mechanism. It will be referred to as a waterproof cover or a waterproof limb cover.

Preferably, the sealing closure mechanism is a one-way mechanism, to prevent removal of the casing by opening the sealing closure mechanism without rupturing the predefined irreversibly rupturable region.

The casing comprises at least one tearable region such as a tear strip, a tear line, a score line, a perforation or a weakened region; removal of the casing is by means of rupturing the tearable region, thereby tearing the casing open.

It should be noted that, in order to prevent water ingress through a perforation, at least one of the following is true: (1) none of the perforation(s) completely penetrates the casing (2) at least the portion of the casing comprising the perforations comprises at least one underlay, with the underlay sealed to the casing so that the seal completely surrounds the perforated region, and (3) each perforation is filled with a filler, the filler easily separable from at least a portion of the perforation during rupture of the tearable region.

In the prior art, as shown in FIG. 1A-B, the waterproof cover (100, 200) for covering a cast comprises a casing (110) with either a single opening (FIG. 1A) or two openings (FIG. 1B). The openings (1020) are sealably closeable to prevent ingress of water or other liquids during use. In FIGS. 1A-B, the opening comprises an elastic band; the waterproof cover is emplaced by pulling the on the elastic so that it opens more widely, lifting the enlarged opening over the cast (or other area to be covered) and releasing the elastic so that the opening closes sealingly around the limb. Removal is by reversing the procedure, by pulling the elastic so as to enlarge the opening, lowering the opening over the area to be uncovered, and releasing the elastic after the waterproof cover has been removed from the limb or other area to be covered. If a modicum of care is taken so that neither the waterproof cover nor the elastic is damaged during removal, the waterproof cover can be reused many times. The terms "opening(s)" and "open end" are used herein interchangeably.

Figure 2A:
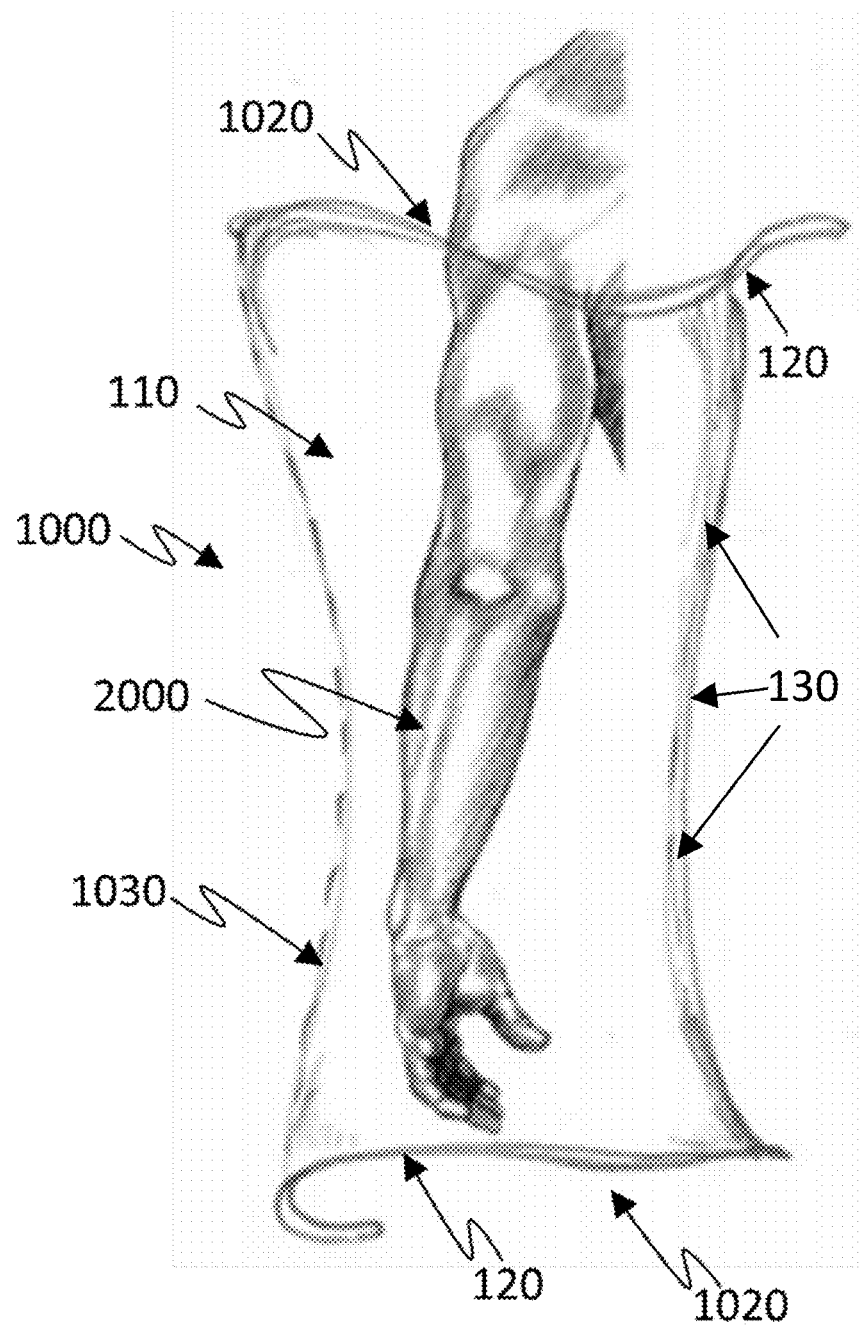
FIGS. 2A-B and 3A-3F schematically illustrate embodiments of the waterproof cover of the present invention.
Figure 2B:
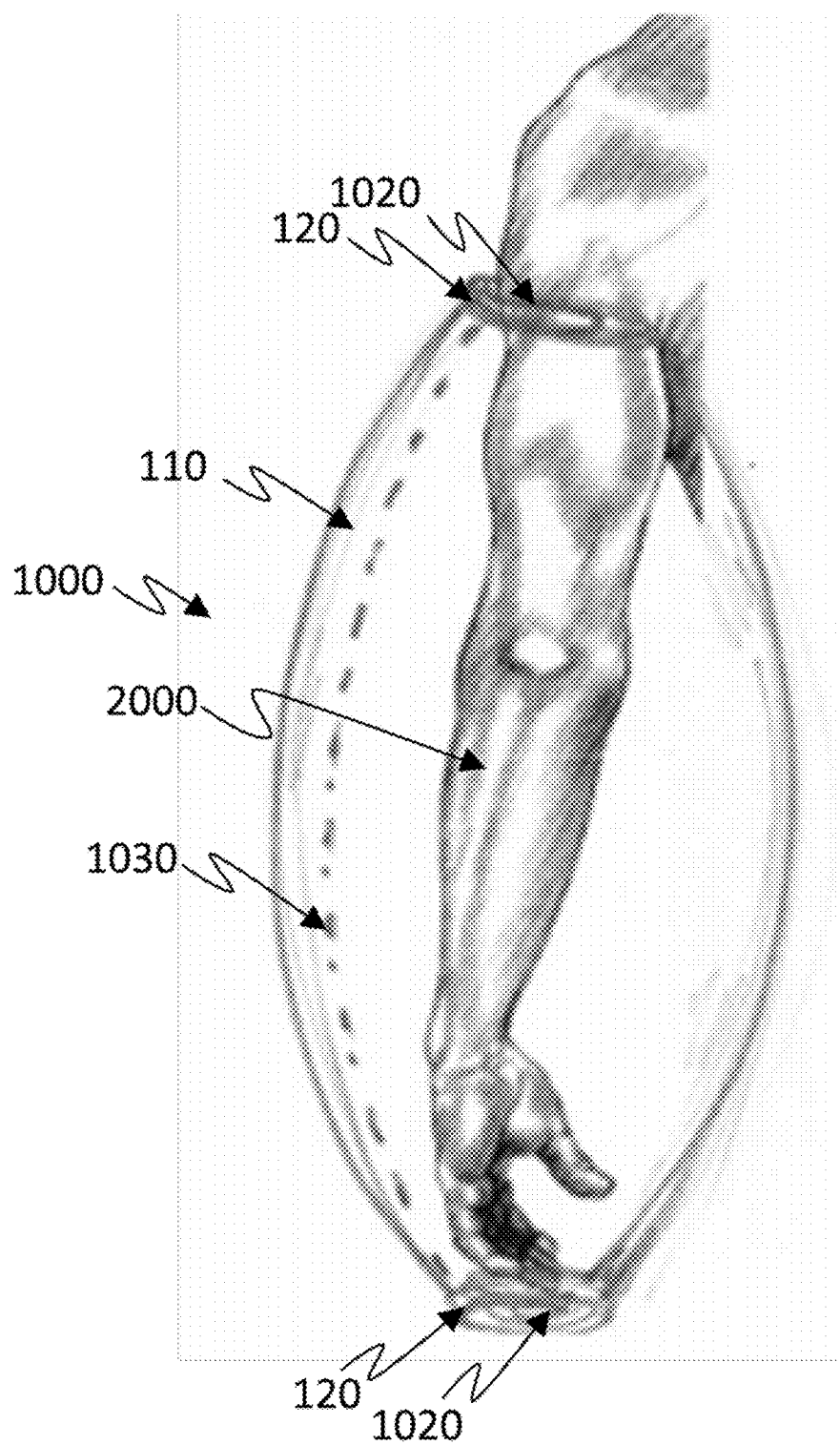

FIG. 2A-B shows a schematic illustration of an embodiment of the waterproof cover (1000) of the present invention, in place on a limb (2000). The waterproof cover (1000) of the present invention comprises a flexible casing (110) with at least one opening (1020), each opening sealably closable by a sealing closure mechanism (120), and at least one predefined irreversibly rupturable region (1030). In the embodiments shown, the waterproof cover (1000) comprises a single predefined irreversibly rupturable region (1030); in other embodiments (not shown), there is more than one predefined irreversibly rupturable region (1030).

FIG. 2A shows the embodiment before use, while FIG. 2B shows the embodiment during use. As shown in FIG. 2A, before use, the flexible casing (110) comprises a flat sheet with a sealing closure mechanism (120) at the top and bottom edges, which will comprise the openings (1020) in use. At least one side edge comprises a one-way mechanism (130) (e.g., an adhesive layer); at least one longitudinal strip comprises a predefined irreversibly rupturable region (1030).

FIG. 2B shows the embodiment during use. The side edge has been sealed and the sealing closure mechanisms (120) have been sealed to the limb (2000).

In some embodiments (not shown), additional sealable openings can allow a finger, a thumb and any combination thereof, or one or more toes to extend outside the waterproof cover. In some embodiments (not shown) at least one side opening allows temporary access to the interior of the casing (110). Such a side opening could allow a medical professional to inspect or treat a wound or lesion in the region enclosed by the casing (110).

In some embodiments, at least one opening (1020) comprises more than one sealing closure mechanism (120).

The casing (110) is impermeable to a liquid selected from a group consisting of a hydrophilic liquid, a lipophilic liquid, a hydrophobic liquid and any combination thereof. Preferably, the casing (110) is also impermeable to at least some emulsions and creams. Preferably, the casing (110) is impermeable to at least weak acids. Preferably, the casing (110) comprises medical-grade materials.

Preferably a majority of the casing (110) is flexible.

Typically, the casing comprises a material selected from a group consisting of polyvinyl chloride, polyurethane, polyethylene including high density polyethylene (HDPE), polyethylene terephthalate, polypropylene, polystyrene and any combination thereof.

Each opening comprises at least one sealing closure mechanism. The sealing closure mechanism can be an elasticated region, a fastenable string or tape, a diaphragm seal, an inflatable cuff, a vacuum ring, an adhesive region, or any other conventional means of sealing a casing so as to prevent ingress of liquid into the casing interior during use and any combination thereof. Preferably, end openings seal against the skin and side openings seal against the casing; preferably, resealing of a side opening does not necessitate contact between the temporary-access side opening and a bandage, a cast, the skin or another item within the casing.

Preferably, a sealing closure mechanism for an end opening comprises a one-way mechanism, so that the sealing closure mechanism is not reversible; it cannot be reopened after closure. This prevents removal of the waterproof cover without damaging it. Where a reversibly closable sealing closure mechanism would allow removal of the waterproof cover undamaged by re-opening the sealing closure mechanism, a one-way mechanism necessitates removal of the waterproof cover by tearing the predefined irreversibly rupturable region or otherwise damaging the waterproof cover beyond usability.

Non-limiting examples of a one-way mechanism for an elasticated region, a fastenable string and a fastenable tape include a one-way ratchet and pawl, a one-way gear track and pawl, a one-way hook and loop and any combination thereof. An inflatable cuff and a vacuum ring can comprise a one-way valve; after filling, either the valve must be removed or the cuff material damaged to release the gas within. A permanent adhesive can also be used with an elasticated region, a fastenable string and a fastenable tape. For an adhesive adhered to the body, a release layer between the waterproof cover and the adhesive can ensure that the removed waterproof cover no longer comprises the adhesive. If the release layer has a higher affinity for the adhesive than for the casing material, the adhesive can be removed from the body along with the release layer. For a hook and loop closure, a one-way mechanism can comprise a pressure-sensitive adhesive surround to the hook and loop region, a pressure-sensitive adhesive in the loop portion of the hook and loop, at least one snap-fit mechanism in or near the hook and loop region and any combination thereof Preferably, a side opening is configured such that it is not possible to remove the waterproof cover via the side opening without opening the predefined irreversibly rupturable region or otherwise damaging the waterproof cover beyond usability.

The waterproof cover is configured to be removable only after it has received sufficient damage, preferably in the predefined irreversibly rupturable region. The predefined irreversibly rupturable region is typically a tear strip, a tear line, a score line, a perforation or a weakened region. Preferably, the predefined irreversibly rupturable region extends to an edge of the waterproof cover so that the entire waterproof cover can be removed as a unit.

Preferably, a tear strip remains attached to the casing in at least one area after tearing so that the waterproof cover and tear strip are necessarily disposable as a unit.

In some embodiments, the tear strip comprises an insert of a material different from that of the casing material. Preferably, the insert is of a material stronger, stiffer or both than the casing material. Preferably, the insert is not detachable from the casing, remaining attached to the main portion of the casing after tearing at at least one location. In some embodiments, the insert is of a material more elastic than the casing material.

In some embodiments, the material in a predefined irreversibly rupturable region is thinner than the material in the main body of the waterproof cover. In some embodiments, the predefined irreversibly rupturable region comprises a material with a lower tear strength than the material in the main body of the waterproof cover.

In some embodiments, the waterproof cover comprises a tag, ring or other protrusion in or near a predefined irreversibly rupturable region; pulling on the tag can rupture material in the predefined irreversibly rupturable region, starting the tear.

In variants of embodiments where a predefined irreversibly rupturable region extends to an edge of the waterproof cover, the waterproof cover comprises a notch or gap at the edge, at or near the predefined irreversibly rupturable region. Separating the edges of the notch or gap can start tearing of the predefined irreversibly rupturable region.

In some embodiments, the waterproof cover comprises more than one predefined irreversibly rupturable region. In some variants of these embodiments, the tear strip comprises at least one pair of predefined irreversibly rupturable regions and the cover material between them.

Figure 3A:
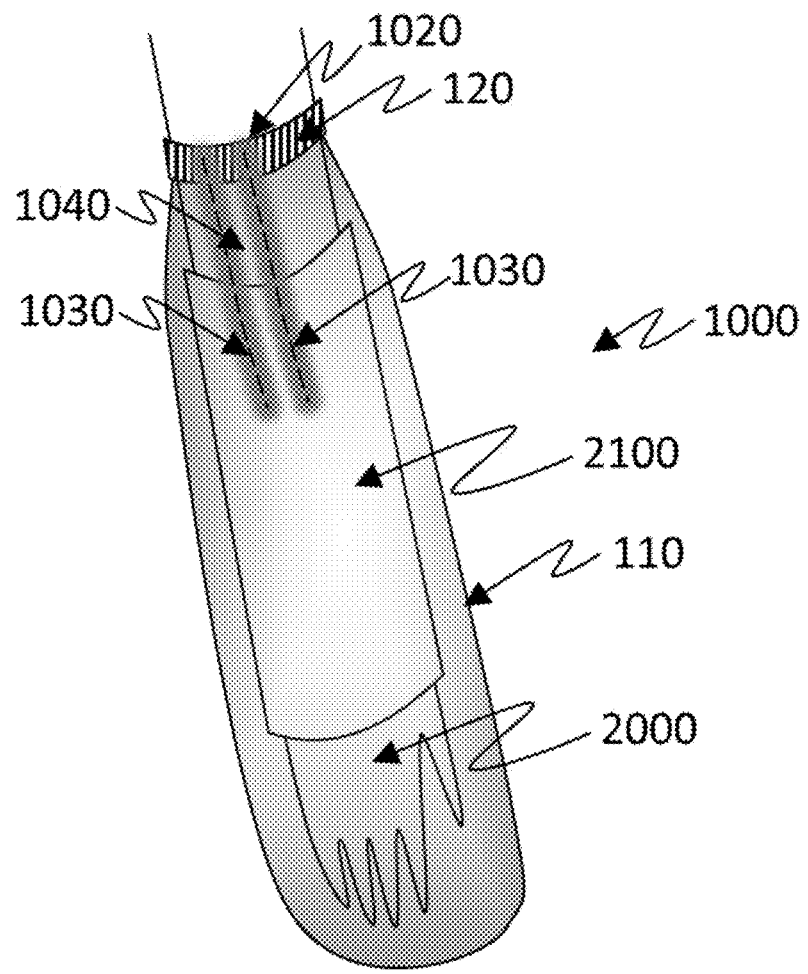
Figure 3B:
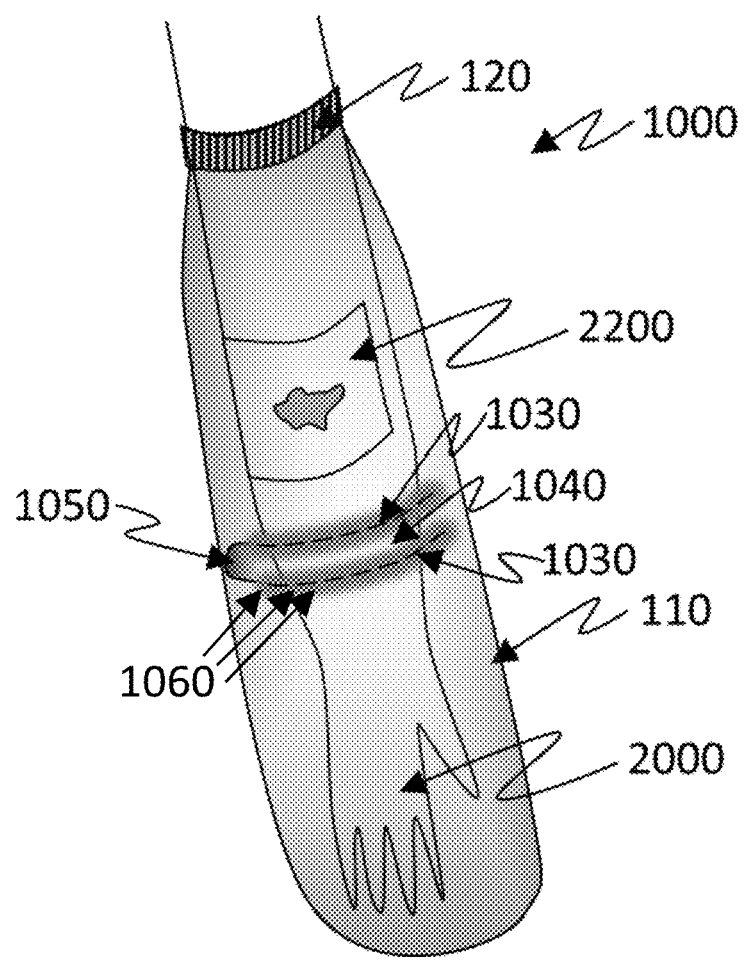

FIG. 3A-B schematically illustrates embodiments of the waterproof cover (1000) comprising a casing (110) with a tear strip (1040). For illustrative purposes, the waterproof cover (1000) is disposed over an arm (2000). In FIG. 3A, for illustrative purposes, there is a cast (2100) on the arm (2000), while in FIG. 3B, the arm (2000) has a wound covered by a bandage (2200). in both FIG. 3A and FIG. 3B, the tear strip (1040) comprises two predefined irreversibly rupturable regions (1030).

In FIG. 3A, the tear strip (1040) reaches the edge of the sealing closure mechanism (120). In this variant embodiment, pulling on the tear strip and rupturing the irreversibly rupturable regions (1030) destroys the sealing closure mechanism (120) and prevents reuse of the waterproof cover (1000).

In FIG. 3B, the tear strip (1040) is in the body of the casing (110) and comprises a pull tab (1050) with a distal end either free of the casing (110) or easily separable from the casing (110). Pulling on the pull tab (1050) causes rupture of the irreversibly rupturable regions (1030) and causes a tear initiator (1060), e.g., a gap, which at least partially separates the two ends of the casing (110), thus destroying the integrity of the casing (110) and preventing reuse of the waterproof cover (1000).

Embodiments of the waterproof cover (1000) can have any combination of individual irreversibly rupturable regions (1030), pairs of irreversibly rupturable regions (1030) forming tear strips (1040) and multiple irreversibly rupturable regions (1030) forming tear strips (1040) or other removable areas. An irreversibly rupturable region (1030) can be at any angle to the edge of an opening, and at any angle to a longitudinal axis of the casing (110). An irreversibly rupturable region (1030) can subtend any radial angle from 0 (along a longitudinal axis of the waterproof cover (1000)) to 360°. If the radial angle is 360° with a single irreversibly rupturable region (1030) lying in a plane perpendicular to the main longitudinal axis of the waterproof cover (1000), rupturing the irreversibly rupturable region (1030) will separate the waterproof cover (1000) into two disjoint halves. A similarly aligned tear strip will separate the waterproof cover (1000) into three disjoint parts, a first casing portion, the tear strip and a second casing portion.

However, if the radial angle is 360° but the single irreversibly rupturable region (1030) lying in a plane not perpendicular to the main longitudinal axis of the waterproof cover (1000), rupturing the irreversibly rupturable region (1030) will leave the waterproof cover (1000) as a unit, with a first casing portion joined to the second casing portion by a diagonal strip.

Figure 3C:
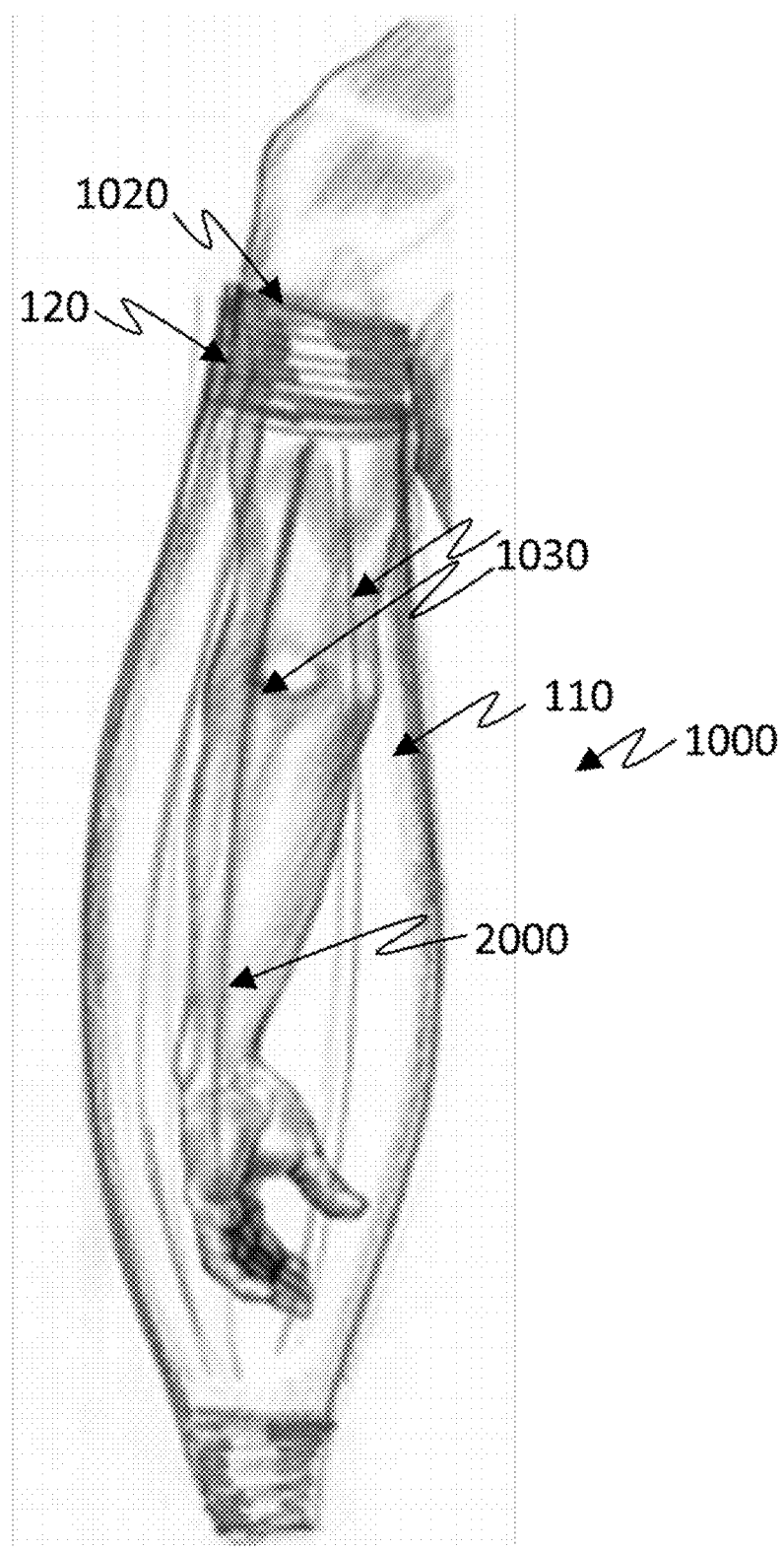

FIG. 3C illustrates an embodiment of the waterproof cover (1000), shown in place over a limb (2000), which comprises two longitudinal irreversibly rupturable regions (1030), extending from near the open end (1020) to near the closed end. The open end (1020) comprises a closure mechanism (120).

Figure 3D:
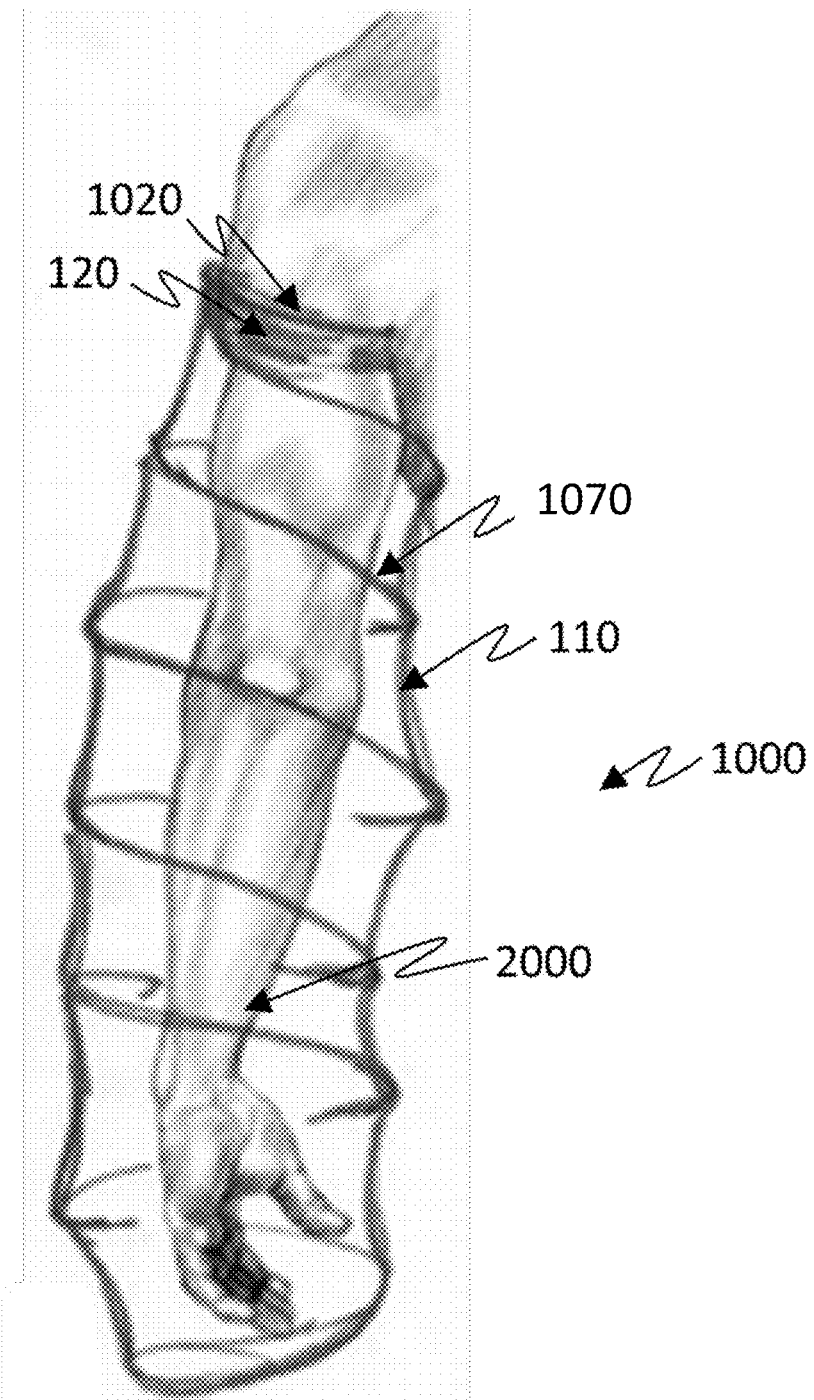
Figure 3E:
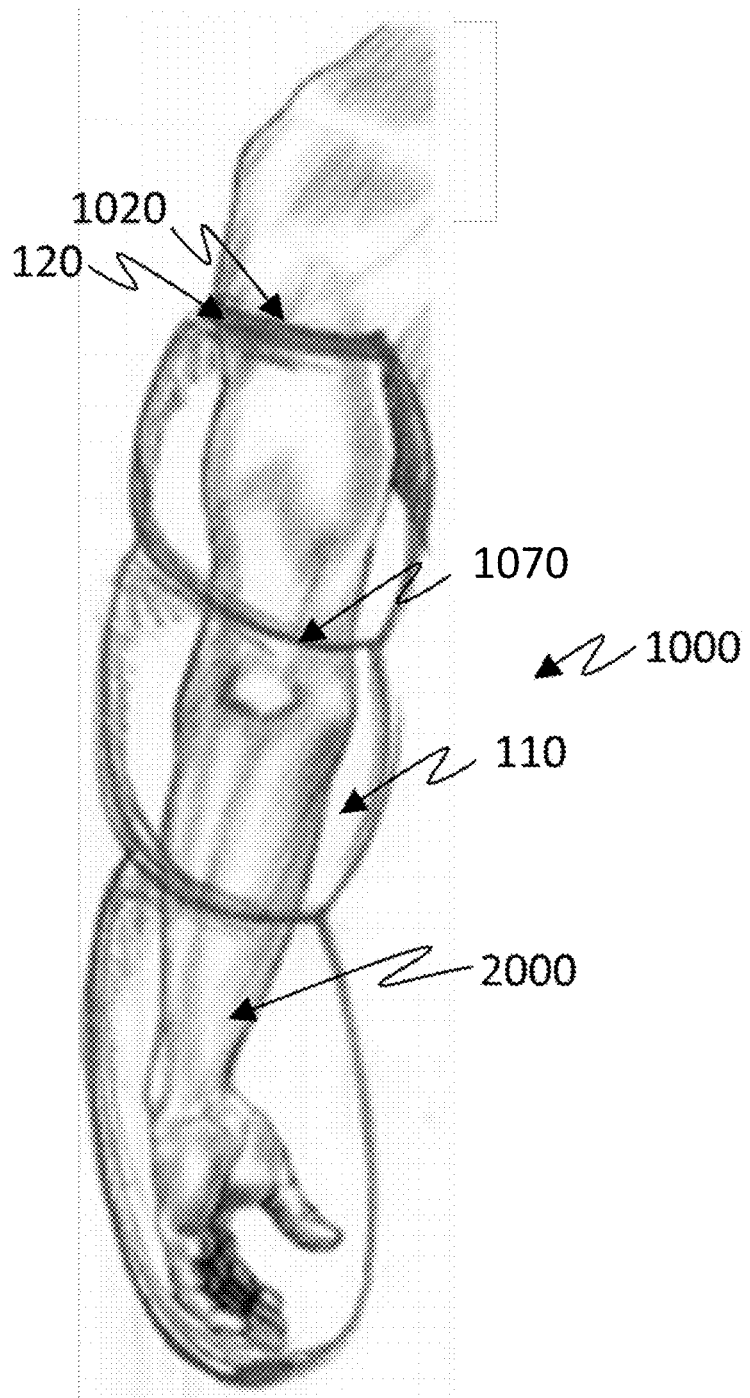
Figure 3F:
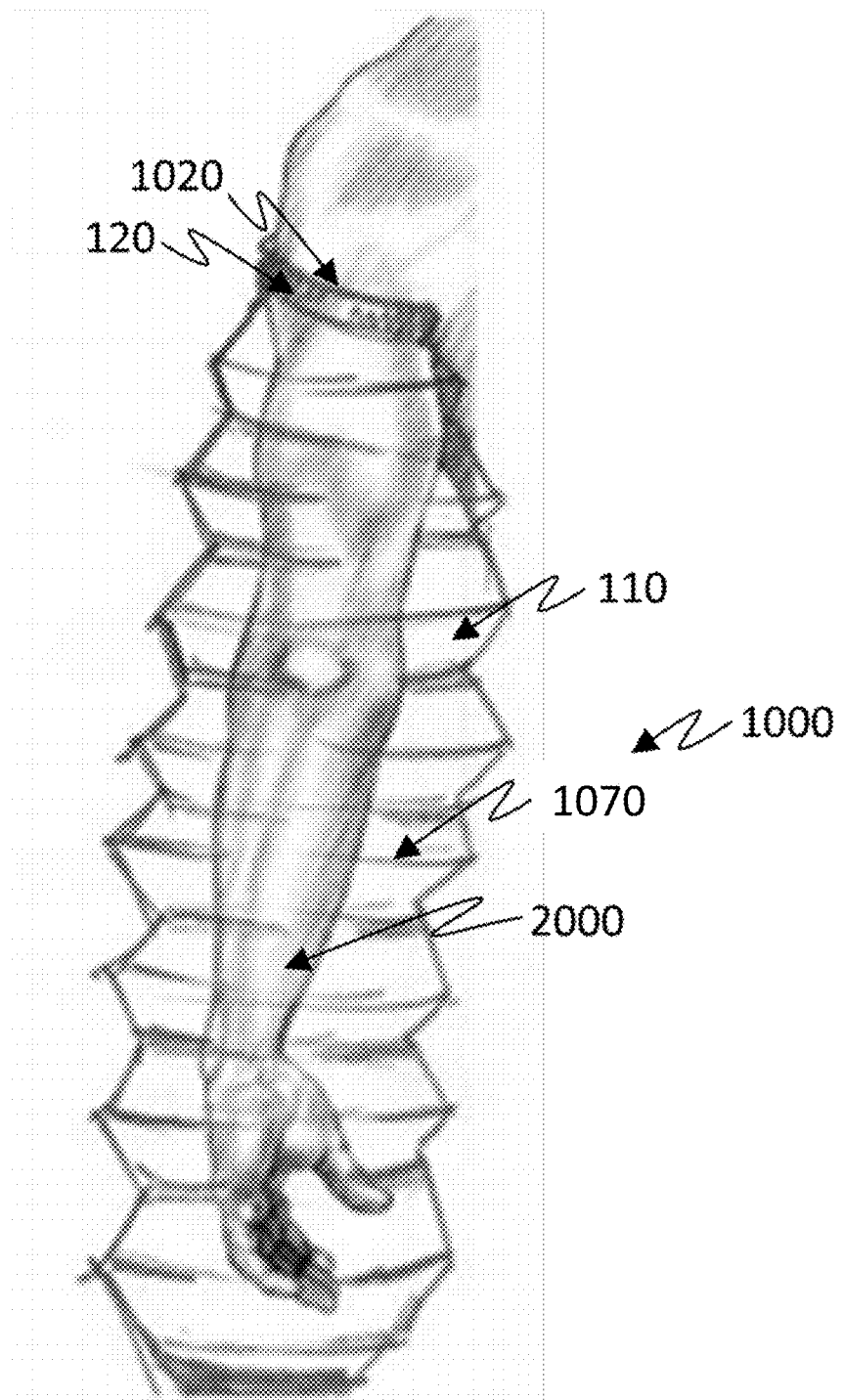

FIGS. 3D-F illustrate embodiments of the waterproof cover (1000) which have one closed end and a sealing closure mechanism (120) at the one open end (1020), and which comprise a stiffening mechanism (1070) configured to keep the casing (110) away from the limb (2000). The stiffening mechanism (1070) is attached, preferably permanently, to the casing (110). The stiffening mechanism can comprise any relatively stiff, but not rigid, material, typically, for non-limiting example, a steel spring, a plastic strip, or a metal wire. The stiffening mechanism (1070) can form a part of the irreversibly rupturable region (1030), so that removal of the stiffening mechanism (1070) ruptures the casing (110) and allows removal of the waterproof cover (1000) from the limb (2000). In other embodiments, the irreversibly rupturable region (1030) can be independent of the stiffening mechanism (1070).

In FIG. 3D, the stiffening mechanism (1070) comprises a spiral of the relatively stiff material.

In FIG. 3E, the stiffening mechanism (1070) comprises a plurality of loops, with the loops being of substantially the same size.

In FIG. 3F, the stiffening mechanism (1070) comprises a plurality of loops, with the loops having a plurality of sizes. In the embodiment shown, the loops are of two sizes, alternately larger and smaller, so that the waterproof cover (1000) has an accordion-like form. In other variants of this embodiment, the loops are graduated in size so that the waterproof cover (1000) is larger at one end than at the other.

The invention claimed is:

1. A waterproof limb cover (1000) for preventing liquid ingress to a predefined region of a limb (2000) in a cast, comprising:
    a casing (110) impermeable to said liquid, said casing (110) comprising at least one opening (1020), said at least one opening (1020) for insertion of said limb (2000), said opening (1020) comprising at least one sealing closure mechanism (120) configured to sealingly enclose said predefined region of said limb (2000);
    said waterproof limb cover (1000) further comprises at least one predefined irreversibly rupturable region (1030) for removal of said waterproof limb cover (1000) from said predefined region of said limb (2000),
    said at least one sealing closure mechanism (120) is a one-way mechanism (130), that prevents removal of said casing (110) by opening said sealing closure mechanism (120) without rupturing said predefined irreversibly rupturable region (1030),
    said sealing closure mechanism (120) comprises a member selected from a group consisting of an elasticated region, a fastenable string or tape, an adhesive region, and any combination thereof,
    wherein at least a first predetermined portion of said at least one predefined irreversibly rupturable region (1030) is on said casing (110); at least a second predetermined portion of said at least one predefined irreversibly rupturable region (1030) is on said opening (1020); and said removal of said waterproof limb cover (1000) irreparably damages both said casing (110) and said opening (1020), allowing only one-time use of said waterproof limb cover (1000).

2. The waterproof limb cover of claim 1, wherein said casing (110) comprises a material selected from a group consisting of polyvinyl chloride, polyurethane, polyethylene, polyethylene terephthalate, polypropylene, polystyrene, a printable material, a pigmentable material, a texturable material, a scorable material and any combination thereof.

3. The waterproof limb cover of claim 1, wherein said casing (110) is configured to display at least one indicia, said indicia selected from a group consisting of: a logo, a name, a patient datum, a hospital datum, a ward indicator, a location indicator, a best-before indicator, a picture, an illustration and any combination thereof.

4. The waterproof limb cover of claim 1, wherein rupture of at least one of said at least one predefined irreversibly rupturable region (1030) ruptures at least one of said at least one sealing closure mechanism (120).

5. The waterproof limb cover of claim 1, wherein said at least one predefined irreversibly rupturable region (1030) comprises at least one member of a group consisting of a tear strip (1040), a tear line, a score line, a perforation and a weakened region.

6. The waterproof limb cover of claim 5, wherein said at least one predefined irreversibly rupturable region (1030) is a tear strip (1040), and said tear strip (1040) remains attached to said waterproof limb cover (1000) in at least one area after tearing, said waterproof limb cover (1000) and said tear strip (1040) being necessarily disposable as a unit.

7. The waterproof limb cover of claim 5, wherein said at least one predefined irreversibly rupturable region (1030) is a tear strip (1040), and said tear strip (1040) comprises an insert of a material having at least one property with a value different from a same property of a material of said casing.

8. The waterproof limb cover of claim 7, wherein said at least one property of said insert is selected from a group consisting of a greater stiffness than a material of said casing, a greater strength than a material of said casing, a greater elasticity than a material of said casing and any combination thereof.

9. The waterproof limb cover of claim 5, wherein said at least one predefined irreversibly rupturable region (1030) is a weakened region, and said weakened region consists of a member of a group consisting of a region with thinner material than a material of said casing 1, a region of material with a lower tear strength than a material of said casing, and any combination thereof.

10. The waterproof limb cover of claim 1, wherein said waterproof limb cover (1000) comprises, in or near at least one of said at least one predefined irreversibly rupturable region (1030), a pullable member selected from a group consisting of a tag, a ring, a protrusion and any combination thereof and pulling on said pullable member ruptures at least a portion of said predefined irreversibly rupturable region (1030).

11. The waterproof limb cover of claim 1, wherein at least one edge of said waterproof limb cover (1000) comprises, in or near at least one of said at least one predefined irreversibly rupturable region (1030), a tear initiator (1060) selected from a group consisting of a notch, a gap and any combination thereof.

12. The waterproof limb cover of claim 11, wherein separation of edges of said tear initiator (1060) initiates tearing of said at least one of said at least one predefined irreversibly rupturable region (1030).

13. The waterproof limb cover of claim 1, wherein said waterproof limb cover (1000) is providable in a packaging selected from a group consisting of aseptic packaging and sterile packaging.

14. The waterproof limb cover of claim 1, wherein said casing (110) comprises a stiffening mechanism (1070), configured to keep said casing (110) away from said limb (2000), said stiffening mechanism (1070) comprises a plurality of metal loops, plastic loops, or both.

15. A waterproof limb cover (1000) for preventing liquid ingress to a predefined region of a limb (2000) in a cast of a non-human animal, comprising: a casing (110) impermeable to said liquid, said casing (110) comprising at least one opening (1020), said at least one opening (1020) for insertion of said limb (2000), said opening (1020) comprising at least one sealing closure mechanism (120) configured to sealingly enclose said predefined region of said limb (2000);

said waterproof limb cover (1000) further comprises at least one predefined irreversibly rupturable region (1030) for removal of said waterproof limb cover (1000) from said predefined region of said limb (2000);

said at least one sealing closure mechanism (120) is a one-way mechanism (130), that prevents removal of said casing (110) by opening said sealing closure mechanism (120) without rupturing said predefined irreversibly rupturable region (1030), said sealing closure mechanism (120) comprises a member selected from a group consisting of an elasticated region, a fastenable string or tape, an adhesive region, and any combination thereof, wherein at least a first predetermined portion of said at least one predefined irreversibly rupturable region (1030) is on said casing (110); at least a second predetermined portion of said at least one predefined irreversibly rupturable region (1030) is on said opening (1020); and said removal of said waterproof limb cover (1000) irreparably damages both said casing (110) and said opening (1020), allowing only one-time use of said waterproof limb cover (1000).

16. The waterproof limb cover of claim 15, wherein said at least one predefined irreversibly rupturable region (1030) comprises at least one member of a group consisting of a tear strip, a tear line, a score line, a perforation and a weakened region.

17. The waterproof limb cover of claim 15, wherein said casing (110) comprises a stiffening mechanism (1070), configured to keep said casing (110) away from said limb (2000), said stiffening mechanism (1070) comprises a plurality of metal loops, plastic loops, or both.

* * * * *